United States Patent [19]

Higgins et al.

[11] Patent Number: 5,479,932
[45] Date of Patent: Jan. 2, 1996

[54] INFANT HEALTH MONITORING SYSTEM

[76] Inventors: Joseph Higgins, 243 Branford Rd., N. Branford, Conn. 06471; E. Carr Everbach, 2103 Mt. Vernon St., Philadelphia, Pa. 19130; Kevin J. Parker, 340 Howland Ave., Rochester, N.Y. 14620

[21] Appl. No.: 106,553

[22] Filed: Aug. 16, 1993

[51] Int. Cl.⁶ .................................................. A61B 5/0205
[52] U.S. Cl. .......................... 128/671; 128/721; 128/670
[58] Field of Search .................................. 128/670, 671, 128/721, 722; 340/573, 665

[56] References Cited

U.S. PATENT DOCUMENTS

| | | | |
|---|---|---|---|
| 4,320,766 | 3/1982 | Alihanka et al. | 128/671 |
| 4,359,723 | 5/1982 | Cohen | 340/573 |
| 4,359,726 | 11/1982 | Lewiner et al. | 340/666 |
| 4,403,215 | 9/1983 | Hofmann et al. | 340/573 |
| 4,438,771 | 3/1984 | Friesen et al. | 128/671 |
| 4,509,527 | 4/1985 | Fraden | 128/721 |
| 4,580,575 | 4/1986 | Birabaun et al. | 128/671 |
| 4,851,816 | 7/1989 | Macias et al. | 340/573 |
| 4,862,144 | 8/1989 | Tao | 128/721 |
| 4,895,160 | 1/1990 | Reents | 128/671 |
| 4,966,155 | 10/1990 | Jackson | 128/670 |
| 5,002,060 | 3/1991 | Nedivi | 128/671 |
| 5,038,137 | 8/1991 | Lloyd | 340/573 |
| 5,099,702 | 3/1992 | French | 128/671 |

FOREIGN PATENT DOCUMENTS 9209232  6/1992  WIPO ..................................... 128/671

*Primary Examiner*—Lee S. Cohen
*Assistant Examiner*—Robert L. Nasser, Jr.
*Attorney, Agent, or Firm*—Melvin I. Stoltz

[57] ABSTRACT

Apparatus for effectively and accurately monitoring the health of an infant is realized by simultaneously detecting large motor movement, heart beat and respiration of the infant, and sounding an alarm when an exacting combination of all three signals is not sensed. This integrated combination effectively eliminates false alarms inherent in prior art monitors. Preferably, a passive sensor is placed under, but not in direct contact with, a child for generating a voltage in proportion to the movement of the child. This signal is amplified, filtered and analyzed for the presence of large motor movement, heart beat and respiration. An alarm signal is sounded when all three are not present in the signal.

5 Claims, 6 Drawing Sheets

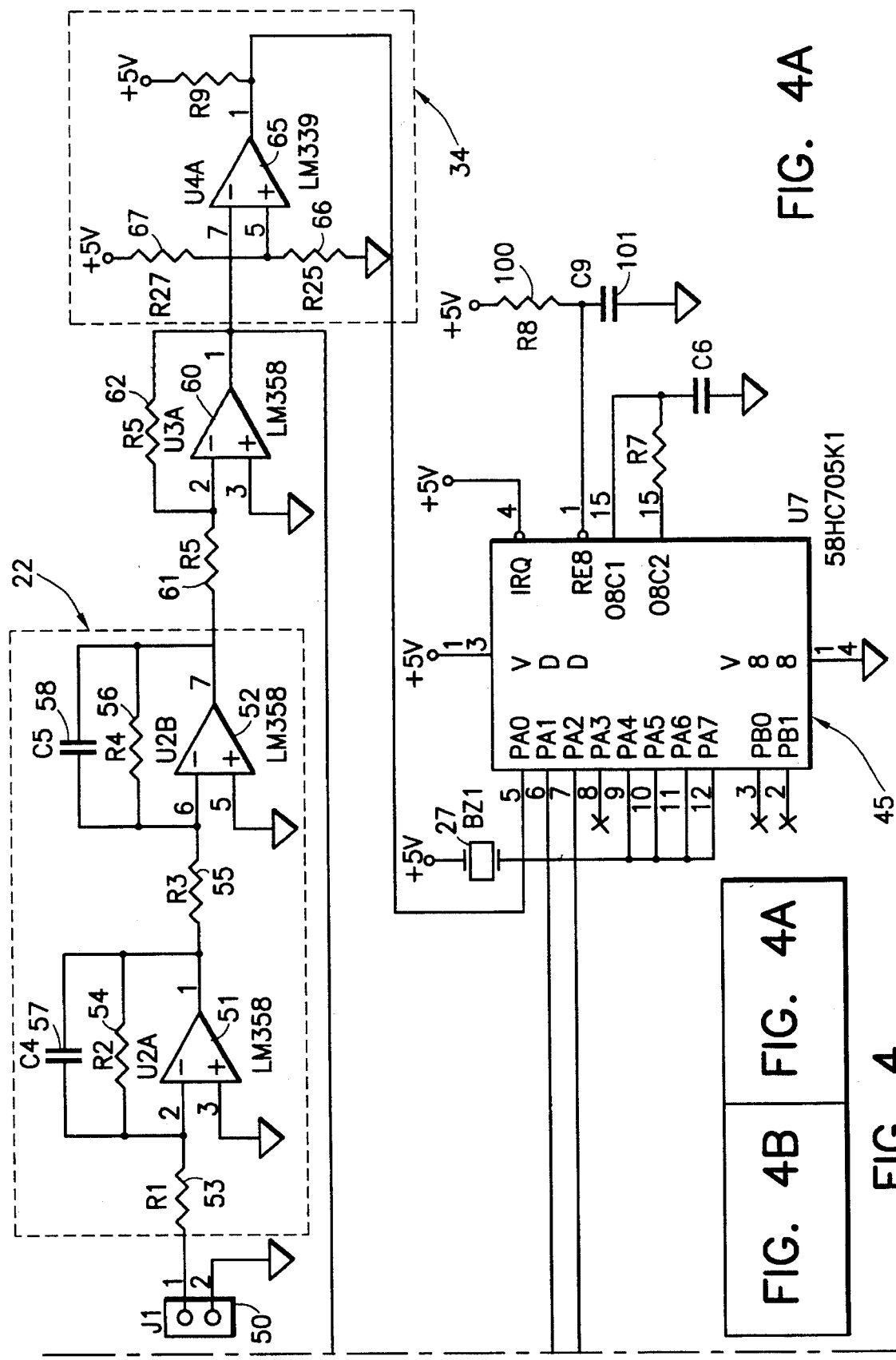

INFANT HEALTH MONITORING SYSTEM

TECHNICAL FIELD

This invention relates to an infant health monitoring system and, more particularly, to an integrated system constructed for simultaneously monitoring three principal health related activities of an infant and sounding an alarm in accordance with a pre-set, protocol.

BACKGROUND ART

For the last several decades, substantial attention has been paid to the problems encountered with Sudden Infant Death Syndrome (SIDS). SIDS has been designated as the highest cause of infant mortality during the first year of life, with one infant dying unexpectedly every hour in the United States. In most cases, SIDS is designated as the cause of death whenever a healthy infant dies suddenly, during sleep, for no apparent reason.

Although SIDS is the most common cause of documented death in children between the ages of one week and one year, with most cases occurring before six months of age, the cause of SIDS remains largely a mystery. Since the infant survival can be achieved if the onset of SIDS is detected, substantial efforts have been expended in developing systems for monitoring an infant's heart rate or breathing rate during sleep. The most prevalent of these prior art systems are commonly referred to as apnea monitors, which monitors the breathing of an infant in order to detect if apnea occurs, which is the cessation of voluntary breathing.

Although monitoring systems were initially developed for hospital use, the continuous monitoring of children in the hospital is not realistic. Consequently, systems for home use have been developed, but have proven to be incapable of providing consistent, uniform and dependable monitoring of a child without suffering from repeated false alarm signals. In view of the high level of anxiety experienced by parents of children who have been determined to be at high risk for SIDS, the repeated generation of false alarms by the monitoring equipment has caused as much anguish in the parents so as to reduce its true efficacy.

In an attempt to reduce the occurrence of false alarms and provide a more dependable monitoring system, several alternate products have been developed for use in the home. These products vary from active monitoring where a sensor is physically in contact with the infant to passive monitors which operate on sensors unconnected to a child. Monitors requiring direct attachment to the infant have fallen out of favor and have not been extensively employed, due to the uncomfortable and potentially dangerous environment created for the child.

U.S. Pat. No. 4,403,218 discloses a respiration monitor for use in detecting apnea which is representative of the construction of monitors of this nature. As is evident from Hoffman as well as similar disclosures, respiration monitors require electrodes to be physically mounted to the infant for monitoring the infant's respiration while asleep. In addition, adjusting the monitor for providing an alarm signal under appropriate conditions is extremely difficult and often not easily attained in a home care environment. Other similar devices are found in U.S. Pat. No. 4,851,816 and the references cited therein.

Prior art attempts have also been made to construct a monitoring system which is passive in nature and does not contact the body of the infant being monitored. One such typical system is found in U.S. Pat. No. 4,438,771. In this patent, the cessation of movement of the infant is monitored with the system being activated whenever total inactivity has been found to occur for a predetermined period of time. Although systems of this nature have been found to be partially effective, they have still suffered from repeated false alarms, as well as being unable to provide the desired monitoring functions under all conditions.

Therefore, it is a principal object of the present invention to provide a health care monitoring system which is employed for monitoring the overall health of an infant while sleeping and producing an alarm signal whenever preset criteria are not met.

Another object of the present invention is to provide an infant health care monitoring system having the characteristic features described above which is constructed for being employed without directly contacting the infant while still being capable of providing repeated, reliable monitoring functions, with virtually no or a minimum of false alarms.

Another object of the present invention is to provide an infant health monitoring system having the characteristic features described above which is employable by individuals in a home environment with simplicity and ease.

A further object of the present invention is to provide an infant health monitoring system having the characteristic features described above which is constructed for both accuracy as well as affordability, thereby allowing most individuals to be able to purchase the monitoring system for home use.

Another object of the present invention is to provide an infant health monitoring system having the characteristic features described above which is capable of simultaneously sensing a plurality of different functions for assuring dependability and effectiveness.

Other and more specific objects will in part be obvious and will in part appear hereinafter.

SUMMARY OF THE INVENTION

By employing the present invention, all of the difficulties and drawbacks found in the prior art have been substantially eliminated and an effective, efficient, and low cost infant health care monitoring system is attained. By employing the present invention, an infant health care monitoring system is provided which is capable of virtually eliminating false alarms, while also providing continuous, accurate monitoring of the overall health of the desired infant.

In the present invention, a single passive sensor is placed in a specific location for monitoring the health of the infant, with that single passive sensor being capable of simultaneously monitoring three separate and independent health related conditions. In particular, it has been found that by simultaneously monitoring an infant's large motor movements, heartbeat, and respiration, the overall health of the infant is continuously scrutinized with a high degree of accuracy and efficacy.

In accordance with the present invention, the single signal produced by the passive sensor is used for determining the existence and/or non-existence of the three health related conditions being monitored, while also assuring that the health related conditions being monitored are within normal ranges. Whenever an anomaly is detected in any one of the three conditions, a signal is generated indicating that a potential alarm condition has been found. However, in the preferred embodiment, the system requires all three conditions to simultaneously register an anomaly situation before an alarm signal will be activated for warning the parent or guardian that a problem may exist. As soon as an anomaly signal is found in all three areas, the alarm signal is promptly activated to bring help to the infant as quickly as possible.

By constructing the health monitoring system of the present invention with the ability to simultaneously monitor three separate and independent activities of the infant, while also requiring anomaly situations to exist in each of the activities being monitored before a signal is generated, false alarms are virtually eliminated, and accurate, consistent and dependable monitoring of the health of the child is provided. Various conditions, situations, or infant positions may exist wherein two of the three health conditions being monitored experience no signal, while the infant is perfectly healthy. Consequently, the achievement of a health monitoring system which simultaneously monitors these three principal health related conditions and requires all three conditions to have non-activity before generating an alarm signal, the user is assured that frustrating and anxiety-promoting false alarms are virtually eliminated.

Furthermore, although three separate and independent health related conditions are being monitored and anomalies must be found in all three areas before an alarm signal is generated, the health monitoring system of this invention is constructed in a manner which requires the existence of a positive signal to assure accurate monitoring and analysis of each of the separate functions. In this way, the user can be certain that whenever two conditions have caused an anomaly to be found, the third circuit is accurately detecting a valid responsive signal within the parameters of the system, thereby assuring that the infant being monitored is healthy and that an alarm condition does not exist.

If desired, the health monitoring system of the present invention may incorporate circuit means for initiating an alarm signal when only two of the three conditions have generated anomaly exiting conditions, even though the third condition monitoring system continues to show normal conditions in existence. In the preferred embodiment, a unique signal would be generated indicating to the user that a potential system error or malfunction may exist and that the system and the infant should be checked. In this way, the anxiety generated by an alarm signal would not be incurred and the parents or guardian of the infant will be able to immediately proceed to both the infant and the system for immediate assessment.

In the preferred embodiment, the single passive sensor comprises a large, flat sheet member formed from material which is constructed in a thin layer or sheet form. In addition, the sensor material is capable of generating a small electrical signal, typically in the millivolt range, whenever pressure is applied to the film or sheet. Preferably, the sensor is formed from polyvinylidene fluoride (PVDF). However, any other similar material may be employed as a substitute, without departing from the scope of the present invention.

By employing a thin layer of PVDF film, or its equivalent, the passive sensor is constructed for placement on the top surface of a mattress or pad in locations such as cribs, bassinets, and playpens. Preferably, the passive sensor is placed between the mattress or pad, with the sheeting material covering the mattress or pad, in order to protect the passive sensor from unwanted and unnecessary exposure to spillage of various fluids. It has been found that even with the passive sensor being positioned below the sheeting material and protective padding, the passive sensor is capable of monitoring all of the desired health related conditions of the infant.

By employing a passive sensor of this nature, the need for using typical prior art sensors affixed to the child is totally obviated. As a result, wire leads going to the child are unnecessary and the child is given complete freedom to move around the crib or playpen without fear of becoming entangled in the monitoring equipment.

Another advantage attained by employing a large, flat passive sensor, formed from such material as PVDF, is the ability to eliminate any need for external electrical excitation of the sensor, as found in prior art systems. This advantage also enables the entire system to operate on battery power, typically nine volts or less. As a result, extremely low levels of electricity are required and greater convenience is attained for the consumer.

In the preferred construction, the signal generated by the sensor is transmitted through a low pass filter and amplifier to reduce electrical noise above the frequencies needed to sense the movement, heartbeat and breathing, while also amplifying the filtered signal. Then, the resulting signal is transmitted to three separate and distinct signal processors, with each signal processor containing circuitry for evaluating the signal and determining whether the particular condition being monitored is present.

In this regard, the amplified and filtered signal received from the sensor is transmitted to a first circuit for monitoring the presence of large motor activities, to a second circuit for monitoring the respiration of the infant, and to a third circuit for monitoring the heartbeat of the infant. Each of these three circuits separately and independently evaluates the signal received in accordance with the parameters established for each circuit.

Typically each circuit receives the signal and filters out the particular signal to be analyzed from the signal received. Then, the filtered signal is analyzed to determine if there is any indication of an anomaly. If an anomaly is found to exist, an anomaly detected signal is transmitted to a condition evaluator. The condition evaluator receives the signals from all three circuits and determines when an alarm signal should be generated. By simultaneously sensing the plurality of different functions, analyzing each function separately, and then processing all three functions simultaneously, a system is achieved which provides dependability and effectiveness.

In constructing a health monitoring system in accordance with this invention, a plurality of alternate circuit constructions and arrangements may be employed to attain the monitoring functions detailed herein. Regardless of the particular circuitry employed for receiving and processing the signals generated by the sensor, it has been found that an effective health monitoring system is attained by employing three independent signal processing circuits, with each particularly constructed for monitoring and analyzing the signal transmitted thereto to evaluate the health condition for which that circuit is constructed. As detailed above, the preferred construction monitors and analyzes for large motor activities, breathing or respiration, and heart rate.

The invention accordingly comprises the features of construction, combinations of elements, and arrangement of parts which will be exemplified in the constructions hereinafter set forth, and the scope of the invention will be indicated in the claims.

THE DRAWINGS

For a fuller understanding of the nature and objects of the present invention, reference should be had to the following detailed description taken in connection with the accompanying drawings, in which.

Figure 2:
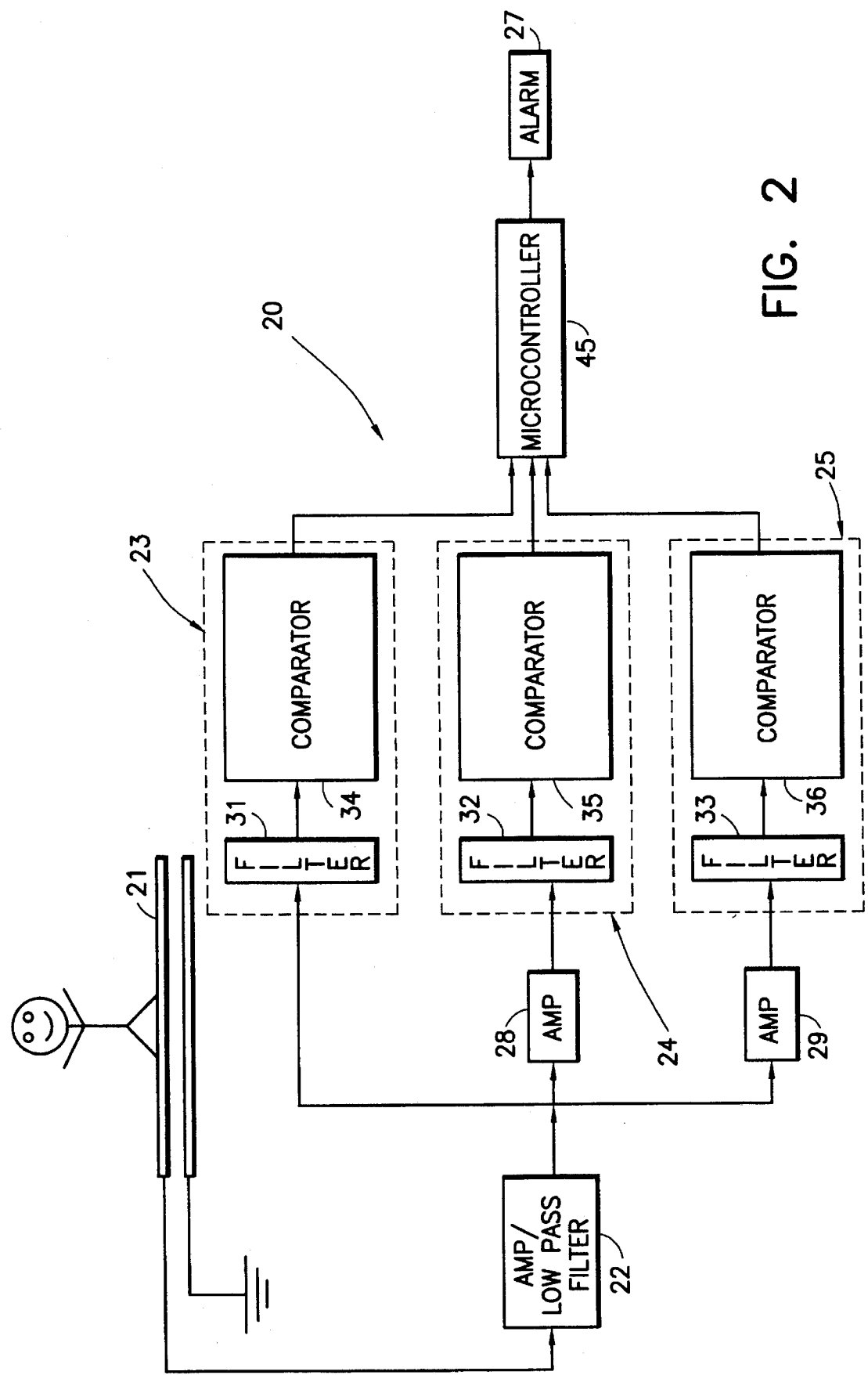
FIGS. 2 and 3 are further functional block diagrams depicting two alternate embodiments for constructing the health monitoring system of the present invention.
Figure 4B:
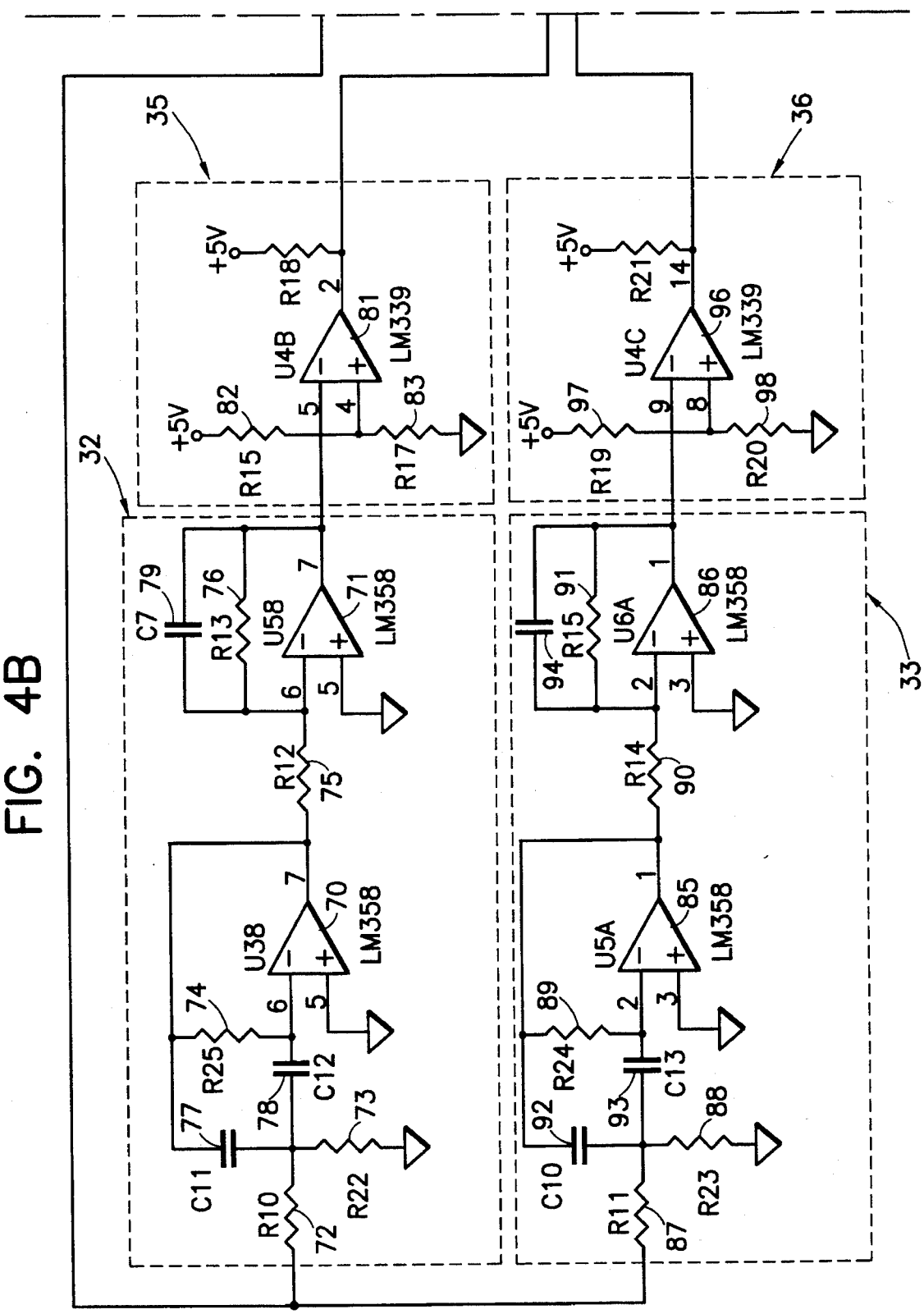
Figure 5:
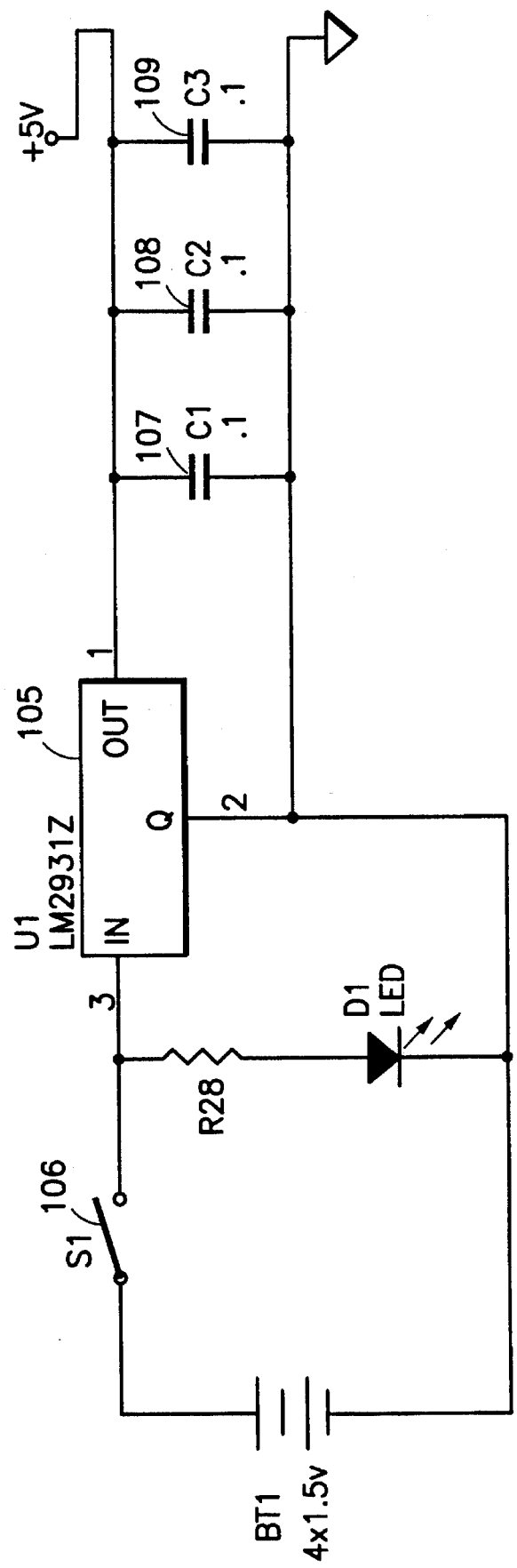

FIG. 4. is a key to the reconstruction of FIGS. 4A & 4B, which are schematic circuit diagrams depicting the preferred electronic construction for the health monitoring system of the present invention in accordance with the system shown in FIG. 2; and FIG. 5 is a schematic circuit diagram depicting the construction of a power supply for use with the circuit of FIG. 4.

DETAILED DISCLOSURE

Figure 1:
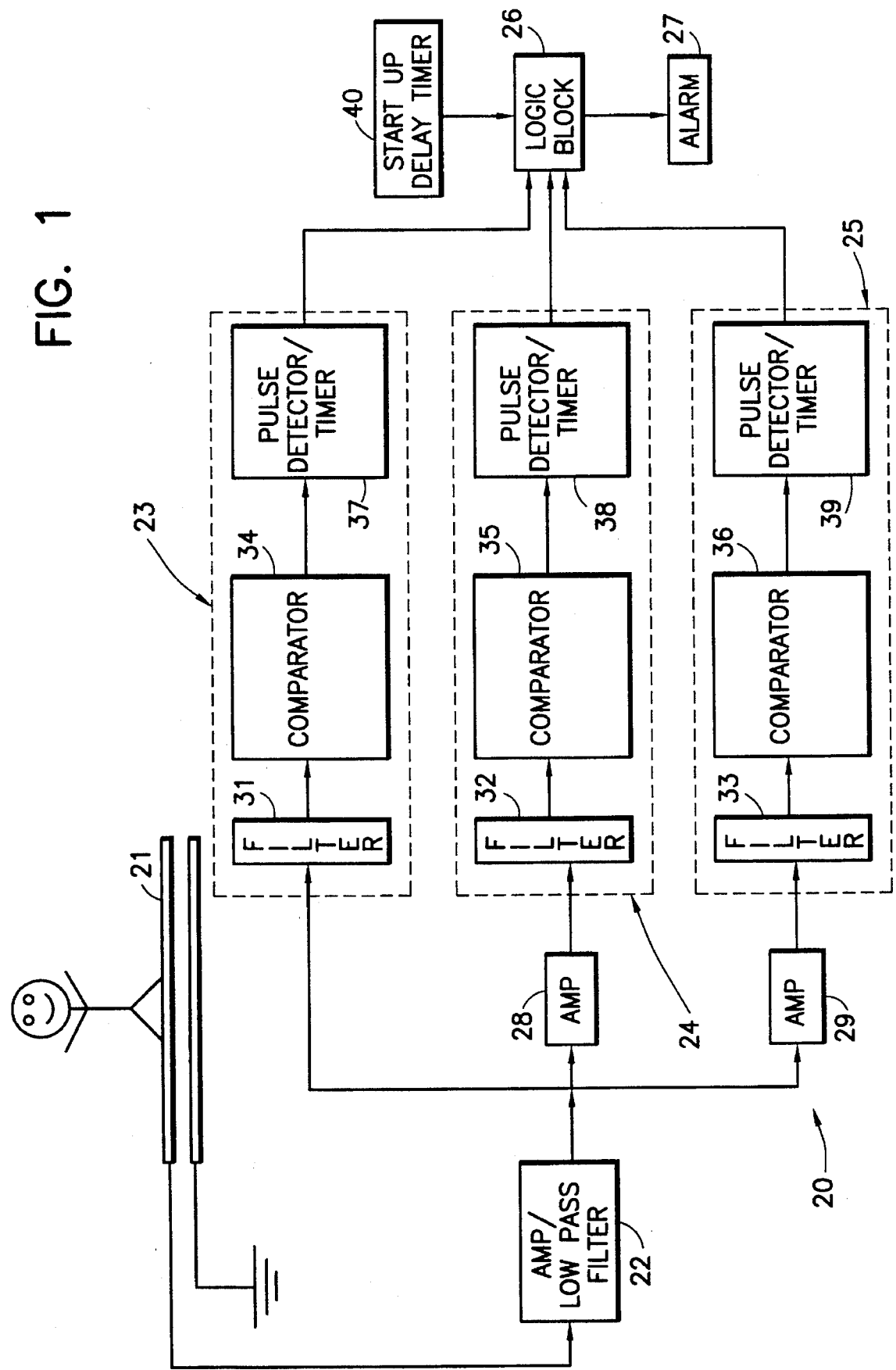
FIG. 1 is a functional block diagram showing the overall operation of one embodiment of the health monitoring system of the present invention.

By referring to FIG. 1, an overall schematic functional block diagram depicting the construction of one embodiment of health monitoring system 20 of the present invention is provided. As shown therein, health monitoring system 20 comprises a passive sensor 21 which is capable of generating a signal in response to the plurality of health related activities of the infant being monitored.

Preferably, the signal generated by passive sensor 21 is transmitted to amplifier and low pass filter 22. Low pass filter/amplifier 22 is constructed to reduce electrical noise above the frequencies needed to sense the three desired health related conditions, while also amplifying the filter signal. The resulting signal is then divided into three separate paths and simultaneously transmitted to three separate and independent condition monitoring and signal processing circuits 23, 24, and 25.

In this embodiment, health monitoring system 20 is completed by providing a logic block 26 which receives the outputs from each of the signal processing circuits and determines when an alarm condition exists. Whenever an alarm condition is found, a signal is transmitted to alarm 27 to initiate the desired warning to alert the parents or guardian of the infant being monitored.

As discussed above, passive sensor 21 preferably comprises a large, flat sheet or film formed from material which is constructed in a thin layer and is capable of generating a small electrical signal, typically in the millivolt range, whenever pressure is applied to the film or sheet. One such material which has been found to provide an effective passive sensor comprises polyvinylidene fluoride (PVDF). In its typical construction, PVDF films comprise, on a microscopic level, a plurality of minute crystallites, each of which behaves as a small electric di-pole, with the di-poles randomly oriented throughout the film. In addition, it is known that above a certain temperature, known as the Curie point, which is about 120° C., the crystallites have no di-pole moment. In manufacturing a film, layer, or sheet, for use as a piezoelectric material for the present invention, a thin sheet or film of the desired material is heated to a temperature just below its Curie point while subjecting the film or sheet to a strong electrical field. By employing this process, all of the di-poles line up with the orientation of the field and, when cooled, with the electrical field removed, the di-poles remain in the polarized position. This polarized position is retained as long as the film or sheet is maintained below its Curie point.

Once constructed in the manner detailed above, the PVDF film or sheet is responsive to the application of a mechanical force, which causes the di-pole moment and the localized crystals to change due to shortening, enlargement, and/or orientation changes. Consequently, any mechanical force causes a deformation of the PVDF film or sheet and results in an overall reduced charge across the PVDF film, proportional to the magnitude and nature of the imposed force. In order to detect an overall induced charge across the PVDF film or layer, at least one electrode must be deposited on each surface of the film or layer, as depicted in FIG. 1.

Since the application of any mechanical force to passive sensor 21 results in an overall induced charge across passive sensor 21 which is proportional to the magnitude and nature of the imposed force, passive sensor 21 can be placed on the mattress, floor, or support pad of an infant's crib, bassinet or playpen and electronically detect and monitor forces corresponding to the infant's large motor activities, breathing rate and heart rate.

As shown in FIG. 1, the signal generated by passive sensor 21 is transmitted to low pass filter and amplifier 22 for amplification of the signal as well as reduction or elimination of electrical noise above the frequencies being monitored. This signal is then split and simultaneously transmitted to three separate monitoring and signal processing circuits 23, 24, and 25. Each processing circuit simultaneously analyzes the incoming signal in accordance with the preset conditions.

In this embodiment, monitoring and signal processing circuit 23 is constructed for monitoring the infant's large motor activities, while processing circuit 24 is constructed for monitoring the breathing or respiration of the infant, with processing circuit 25 constructed for monitoring the heart rate of the infant. In order to assure accuracy and effectiveness, the signal transmitted to processing circuit 24 is preferably first amplified by amplifier 28, while the signal transmitted to processing circuit 25 is amplified by amplifier 29.

Each processing circuit 23, 24, and 25 comprises a filter, a comparator, and a pulse detector/timer. By employing these components, the signal transmitted to each of these processing circuits is capable of being monitored and analyzed to determine whether a normal signal relating to one particular health related condition of the infant has been received by the circuit. Although the incorporation of a filter in each of the processing circuits is preferred, it has been found that the filter is optional in processing circuit 23 in view of the amplitude of the signal being monitored by circuit 23 which analyzes the infant's large motor activities. However, in processing circuits 24 and 25, the incoming signal is filtered through a band pass filter so that only the range of frequencies corresponding to the health condition being monitored will pass through to the comparator.

In this regard, band pass filter 32 of respiration or breathing monitoring and processing circuit 24 receives the signal from amplifier 28 and filters out all frequencies other than the frequencies ranging between the known frequency for an infant's respiration. Although any desired frequency range can be employed, it is preferred to set the frequency for an infant's respiration as ranging between about 25 and 70 respirations per minute. Consequently, frequencies falling within this range are allowed to pass through filter 32 to comparator 35.

Similarly, band pass filter 33 allows the frequencies corresponding to the known range of frequencies for the heart rate of an infant to pass to comparator 36, while filtering out all other frequencies. Although any desired frequency range can be employed, the preferred frequency range for an infant's heart rate has been established at between about 80 and 130 beats per minute. Consequently, this range of frequencies is allowed to pass through filter 33 to comparator 36.

Each of the comparators 34, 35, and 36 receives the signal transmitted thereto and compares the signal to a reference voltage which corresponds to the amplitude of the signal corresponding to the particular health condition being monitored. Whenever the signal transmitted to the comparator exceeds the reference voltage, a signal is outputted to the pulse detector/timer associated therewith in the circuit.

Comparator 34 transmits a signal to pulse detector/timer 37 whenever the signal transmitted to comparator 34 from filter 31, if employed, exceeds the reference voltage representing the amplitude of the signal anticipated for monitoring the large motor activities of the infant. Pulse detector/timer receives the incoming signals from comparator 34 and initiates a timing sequence for each pulse received. Typically, pulse detector/timer 37 resets to zero each time a new pulse signal is received.

By monitoring the output signals from comparator 34 and timing these signals, pulse detector/timer assures that the signals being received by pulse detector/timer 37 are transmitted with sufficient regularity to assure that the infant is active. It has been found that pulse detector/timer 37 should expect to receive a signal from comparator 34 at least once every forty seconds, if the infant is normally active. If this frequency rate is not attained, an anomaly detected signal is transmitted from detector/timer 37 to logic circuit 26. Preferably, the anomaly detected signal is continuously transmitted to logic circuit 26, until a new pulse is received by detector/timer 37.

In processing circuit 24, which monitors the breathing or respiration of the infant, comparator 35 receives the signal from band pass filter 32 and compares the amplitude of the signal received to a reference voltage corresponding to the expected amplitude of a signal corresponding to normal breathing of an infant. Whenever the signal received by comparator 35 exceeds the reference voltage, a pulse detected signal is transmitted to pulse detector/timer 38.

Detector/timer 38 receives the input signal from comparator 35 and times the transmission rate between signals, resetting to zero each time a new signal is received. In monitoring the breathing rate and determining when an alarm signal should be generated, it has been found that a time span of thirty seconds effectively monitors the breathing rate and accounts for any normal anomalies, before a possible alarm condition signal is generated.

As a result, pulse detector/timer 38 receives the output pulse signal from comparator 35, timing each of the pulse signals transmitted thereto. If a new signal is not received within thirty seconds of the previous signal, pulse detector/timer 38 initiates an anomaly detected signal and transmits the signal to logic circuit 26. This signal is preferably maintained until a pulse is received by detector/timer 38.

In heart rate processing circuit 25, the signal from band pass filter 33 is transmitted to comparator 36, wherein the signal is compared to a reference voltage corresponding to the expected amplitude for an incoming signal representing the heart beat of an infant. Each time the incoming signal exceeds the reference voltage level, comparator 36 outputs a pulse to pulse detector/timer 39.

In a similar manner as discussed above, pulse detector/timer 39 receives the incoming signal from comparator 36 and times the period between signals, resetting the timer each time a new signal is received. If a new signal is not received within the predetermined period of time, an anomaly detected signal is transmitted to logic block 26.

In the preferred embodiment, it has been found that the period of time between the receipt of signals representing the heart rate is preferably set at about twenty seconds. Consequently, if more than twenty seconds pass before a new signal is transmitted from comparator 36 to a pulse detector/timer 39, pulse detector/timer 39 transmits an anomaly detected signal to logic block 26, and continues this signal until a new pulse is received by detector/timer 39.

In this embodiment, logic block 26 receives the output signals from pulse detectors/timers 37, 38, and 39 and evaluates the incoming signals to determine when an initiation signal is to be transmitted to alarm 27. In the preferred embodiment, an anomaly detected signal must be received from detector/timers 37, 38 and 39 before an alarm initiation signal is generated by logic block 26. In this way, assurance is provided that all three health related conditions have remained undetected by the monitoring system, simultaneously, for the period of time sampled by each processing circuit. In addition, since each processing circuit immediately terminates an anomaly detected signal whenever a new pulse is received, the presence of three anomaly detected signals at logic block 26 indicates that no new activity has been found in any of the processing circuits.

In addition to initiating an alarm signal when all three processing circuits have transmitted anomaly detected signals to logic block 26, logic block 26 may also be constructed to initiate an alarm signal or a possible malfunction signal in response to other parameters found to be desirable. Although it has been found that the infant health monitoring system of the present invention need not incorporate any such additional system diagnostic circuitry, this additional analysis can be provided if desired.

In the embodiment depicted in FIG. 1, health monitoring system 20 preferably incorporates a start-up delay timer circuit 40 which is controllably connected to logic block 26. In this construction, start-up delay timer 40 deactivates logic block 26 from initiating any alarm signal for a predetermined period of time, whenever health monitoring system 20 has been initially activated. As a result, assurance is provided that all of the components of health monitoring system 20 are properly powered and functional before any alarm signal can be generated. In this way, further assurance is provided that the system will operate in a dependable and efficient manner, with virtually no unwanted false alarm signals being generated.

Figure 3:
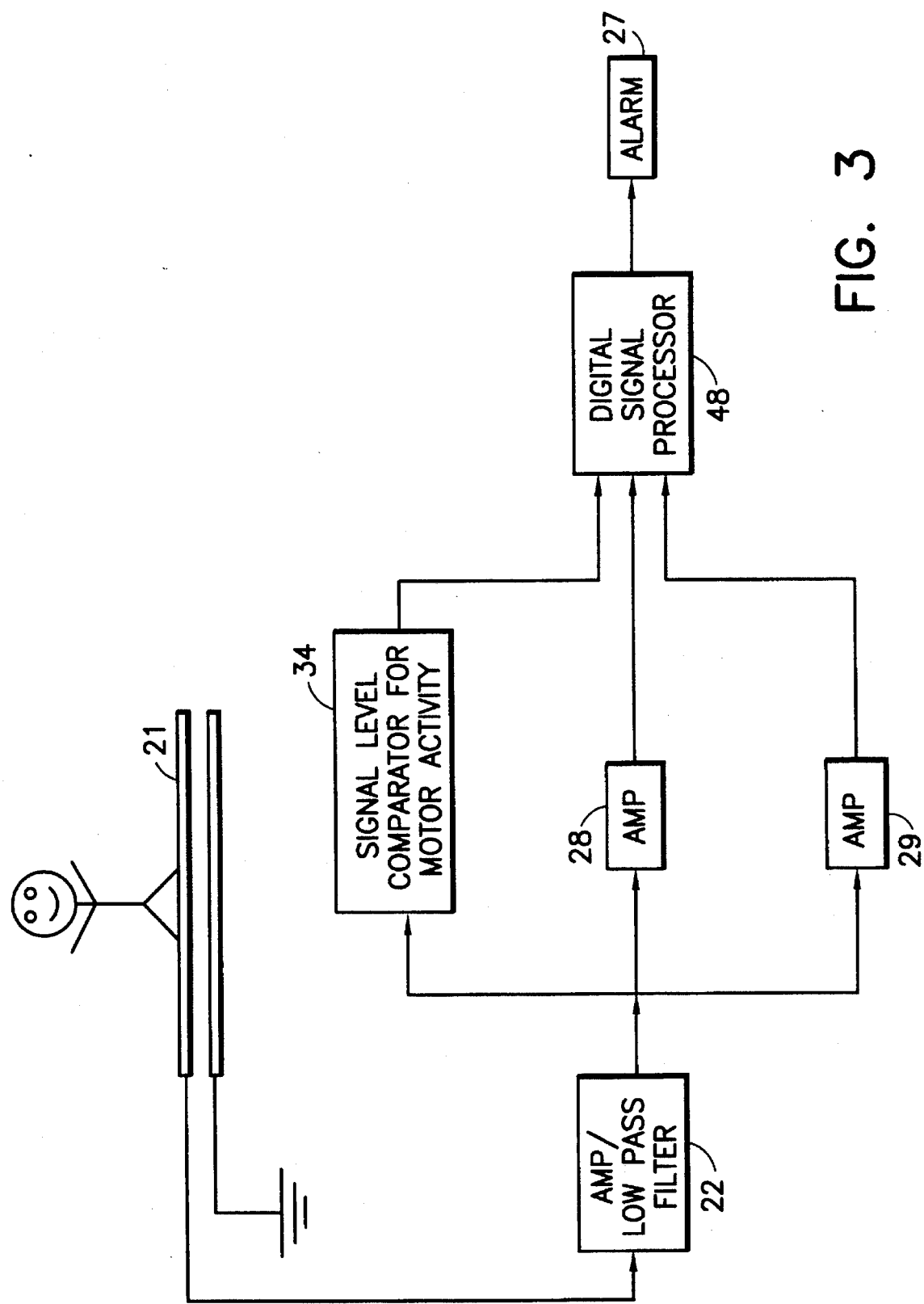

In FIGS. 2 and 3, two additional schematic, functional block diagrams are provided depicting two alternate constructions for health monitoring system 20 of the present invention. In the embodiment depicted in FIG. 2, health monitoring system 20 is constructed substantially similar to the embodiment detailed above in FIG. 1. However, in this embodiment, each of the monitoring and signal processing circuits 23, 24, and 25 each comprise only a filter and a comparator.

As shown in FIG. 2, the output signal from each comparator is transmitted directly to a microprocessor or microcontroller 45. As more fully detailed below, by employing this embodiment, all of the pulse detecting and pulse timing functions are controlled by microcontroller 45, as well as all of the functions previously provided by logic block 26.

Microcontroller 45 operates to receive, process and analyze each of the output signals from the comparator of each of the processing circuits 23, 24, and 25 as well as to determine the conditions under which an alarm signal need be activated. Once such a determination is made, a signal is transmitted to alarm 27 for indicating the existence of an alarm condition.

In the embodiment depicted in FIG. 2, the signal generated by passive sensor 21 is transmitted through low pass filter/amplifier 22 and then split into three parallel paths, as discussed above. In substantially the same way, the path employed for monitoring the infant's large motor activities has the signal transmitted to processing circuit 23. The second signal path, constructed for monitoring the infant's breathing, transmits its signal through amplifier 28 and then to processing circuit 24, while the final signal path, for monitoring the infant's heart rate, is transmitted through amplifier 29 and then to processing circuit 25.

Processing circuit 23 comprises filter 31, if desired, and comparator 34, both of which function in substantially the identical manner detailed above in FIG. 1. Similarly, processing circuit 24 comprises filter 32 and comparator 35, while processing circuit 25 comprises filter 33 and comparator 36. All of these components operate in substantially the identical manner detailed above.

As is apparent from this disclosure, processing circuit 23 analyzes the input signal to determine the infant's large motor activities, while processing circuit 24 monitors and analyzes the infant's breathing or respiration, with processing circuit 25 monitoring and analyzing the infant's heart rate. Whenever comparator 34, 35 or 36 receive an input signal which exceeds the reference voltage level associated with each comparator, the comparator transmits an output pulse signal to microcontroller 45. As discussed above, microcontroller 45 receives each of the input pulse signals, measures the time period between the receipt of each type of signal and analyzes the results to determine when an alarm condition exists.

In the embodiment depicted in FIG. 3, a fully integrated electronic construction is depicted. In this embodiment, passive sensor 21 transmits the resulting signal to low pass filter and amplifier 22 which effectively transmits the resulting signal to a digital signal processor 48. If desired, all of the signal monitoring and analyzing functions detailed above in references to FIGS. 1 and 2 can be performed by digital signal processor 48.

In FIG. 3, an alternate embodiment is disclosed wherein the output of low pass filter and amplifier 22 is split into three parallel paths, as detailed above in FIGS. 1 and 2, with each of these paths representing the three health related functions to be monitored. Although this embodiment of the present invention can be achieved in a variety of alternate constructions, FIG. 3 depicts one particular embodiment wherein one of the output paths of amplifier/filter 22 is transmitted through comparator 34, which is constructed for analyzing the signal related to the infant's large motor activity. In this way, the large amplitude signal representing the infant's motor activity can be analyzed in the manner detailed above, with the output of comparator 34 being transmitted as a pulse signal to digital processor 48 each time the amplitude of the incoming signal exceeds the reference voltage level incorporated within comparator 34. Digital processor 48 receives the incoming pulse signals and measures the time period between these signals to assure the level of activity of the infant complies with the standards incorporated in processor 48.

The remaining two signal transmission paths represent the respiration monitoring paths and the heart rate monitoring paths. As shown in FIG. 3, the path representing the respiration rate is transmitted through amplifier 28, in order to amplify the signal, with the amplified signal being transmitted to digital signal processor 48. Similarly, the remaining signal is transmitted through amplifier 29 to amplify the heart rate signal which is then transmitted to digital signal processor 48.

Digital signal processor 48 receives the output signal from amplifiers 28 and 29 and performs all of the requisite monitoring and analyzing functions required to assure that the respiration rate and the heart rate of the infant are properly sensed. Whenever processor 48 finds that all three health related conditions have simultaneously remained undetected for a time period greater than the requisite threshold, an alarm initiation signal is transmitted to alarm 27 to provide the desired warning.

As is apparent from the foregoing detailed disclosure, the health monitoring system of the present invention can be effectuated in a variety of alternate constructions, while still incorporating the teaching of the present invention As a result, these three alternate constructions, as well as any other alternate constructions consistent with this disclosure is intended to be within the scope of the present invention.

In order to provide an even further disclosure of the present invention in a manner which will clearly enable one of ordinary skill in the art to practice the present invention, reference should be made to FIGS. 4 and 5, along with the following detailed discussion. FIG. 4 provides a detailed circuit diagram depicting the construction of health monitoring system 20 of this invention as diagrammatically represented in FIG. 2. In addition, FIG. 5 provides a circuit diagram showing the general construction of a power supply for use with the circuit of FIG. 4.

As shown in FIG. 4, junction box 50 is employed for receiving the output signal from passive sensor 21 and transmitting the signal to the circuitry for monitoring and analysis. The output signal from passive sensor 21 is transmitted through junction box 50 to low pass filter and amplifier 22. As depicted in FIG. 4, the low pass filter/amplifier 22 employs two operational amplifiers 51 and 52, the gains of which are defined by resistors 53 and 54 and resistors 55 and 56. In addition, capacitors 57 and 58 are employed to eliminate electrical noise from sources such as household appliances as well as signals which may be generated by nearby trucks or trains.

In the embodiment depicted in FIG. 4, the output from low pass filter and amplifier 22 is transmitted to operational amplifier 60, which further amplifies the filtered signal by an amount defined by resistors 61 and 62. The output of amplifier 60 is then split into three parallel paths for analysis of the signal by each of the three independent health monitoring and signal processing circuits. If desired, as depicted in FIG. 2, the output signal from low pass filter/amplifier 22 can be split into three parallel paths with at least two of the paths incorporating separate amplifiers. As an alternate construction, of FIG. 4 depicts the use of a single amplifier 60 for amplifying the output signal from low pass filter/amplifier 22 prior to splitting the signal into the three parallel paths.

By employing the embodiment of the present invention depicted in FIG. 4, the total gain or amplification achieved by amplifiers 51, 52 and 60 is scaled to assure that the respiration and heart beat components of the signal generated by passive sensor 21 do not drive the output signal of amplifier 60 to its maximum amplitude, while allowing the component of the signal generated by the infant's large motor movements (rolling, standing, walking, jumping, etc.) to drive the output of amplifier 60 to its maximum amplitude. In this way, each of the monitoring and signal processing circuits 23, 24 and 25 can best provide the desired accurate signal monitoring and analysis.

The output of amplifier 60 is transmitted to comparator circuit 34 for analyzing the signal to determine the presence of any large motor activity. In performing this analysis, circuit 34 incorporates a comparator 65 which employs a five volt input and resistors 66 and 67 to define a reference voltage to which the input signal from amplifier 60 is compared. If the signal received by comparator 65 from amplifier 60 exceeds the preset reference voltage, comparator 65 transmits an output pulse signal, which represents the detection of a signal corresponding to large motor activity by the infant. This output signal is transmitted to microcontroller/microprocessor 45.

While comparator circuit 34 is performing its analysis of the output from amplifier 60, the same amplified signal is simultaneously transmitted and analyzed by processing circuits 24 and 25. In this embodiment, respiration processing circuit 24 comprises filter 32 and comparator 35. The output signal of amplifier 60 is analyzed for the presence of breathing or respiration by transmitting the signal to filter circuit 32. Filter circuit 32 comprises operational amplifier 70 and 71 in combination with resistors 72, 73, 74, 75, and 76 and capacitors 77, 78, and 79. In this construction, amplifier 70 together with resistors 72, 73, and 74, along with capacitors 77 and 78 form a band pass filter. The values of these resistors and capacitors are selected to pass a range of frequencies for the infant's respiration which corresponds to the conventional frequency for the active respiration by an infant.

As detailed above, the preferred frequency rate for an infant's respiration ranges between 26 and 70 respirations per minute. As a result, the output of the band pass filter stage contains the signals falling within the desired range and is transmitted for further amplification and filtering by a low pass filter stage comprising an amplifier 71, capacitor 79, and resistors 75 and 76. The signal gain of this amplifier is defined by resistors 75 and 76 and the cutoff frequency of the filter is defined by capacitor 79.

The output of filter circuit 32 is transmitted to comparator circuit 35 which incorporates comparator 81 and an input reference voltage for comparator 81 which is defined by a five volt source and resistors 82 and 83. Comparator 81 receives the output from filter 32 on one of its inputs and compares this signal to the reference voltage signal transmitted to its other input. Whenever the input signal from filter 32 exceeds the reference voltage level, comparator 81 transmits a breathing pulse detected signal to microprocessor 45.

The pulse rate monitoring and processing circuit 25 operates substantially identically to the breathing rate processing circuit 24 with the output signal of amplifier 60 being transmitted to filter 33. As shown in FIG. 4, filter 33 incorporates amplifiers 85 and 86, resistors 87, 88, 89, 90, and 91, and capacitors 92, 93, and 94.

In this embodiment, amplifier 85 together with resistors 87, 88, and 89 and capacitors 92 and 93 form a band pass filter, with the values of the resistors and capacitors selected to pass the range of frequencies corresponding to the infant's heart rate. As discussed above, although any desired frequency band can be employed, it has been found that a frequency ranging between about 80 and 130 beats per minute best represents the heart rate of an infant.

The output of this band pass filter stage is further amplified and filtered by a low pass filter stage employing amplifier 86, capacitor 94, and resistors 90 and 91. The signal gain of this low pass filter stage is defined by resistors 90 and 91 with the cutoff frequency defined by capacitor 94.

The output of filter 33 is transmitted to comparator circuit 36 to determine if the signal received properly represents signals corresponding to the heart rate of the infant being monitored. In order to perform this analysis, comparator circuit 36 incorporates a comparator 96 which receives the output of filter 33 at one of its inputs and compares the input signal with a reference voltage level established by a five volt input source and resistors 97 and 98. The reference voltage level provided by the five watt input source and resistors 97 and 98 is selected to define the requisite amplitude of a signal corresponding to the heart rate of an infant. Consequently, whenever the signal transmitted by filter 33 to comparator 96 exceeds the reference voltage level, comparator 36 transmits an output signal to microcontroller 45 indicating the detection of a pulse signal corresponding to the heart rate of the infant.

In the preferred embodiment, microprocessor or microcontroller 45 comprises a self-contained computer incorporating both read only memory and random access memory. In addition, microprocessor 45 is constructed to generate an internal oscillation signal, the frequency of which is used as a time base for all of the functions being performed by microprocessor 45.

As detailed above, the preset program incorporated in microprocessor or microcontroller 45 operates to establish the time duration between the leading edge of the signals received on input pins 5, 6, and 7 of microprocessor 45 which correspond to the inputs being received from large motor activity processing circuit 23, breathing rate processing circuit 24, and heart rate processing circuit 25, respectively. As fully detailed above, microprocessor 45 analyzes each of the input signals received, and times each of the input signals to be certain that the desired activity is being recognized. Whenever all three health conditions being monitored fail to simultaneously transmit an input signal to microprocessor 45, and no signal is received for the predetermined period of time, an alarm initiation signal is transmitted to alarm 27 to sound the warning.

As discussed above, the system preferably incorporates a time delay to be certain that all of the components are properly activated prior to enabling any alarm signal to be generated. In this regard, resistor 100 and capacitor 101 are employed to delay the initiation of the circuitry after the power supply has become stable until all of the components are operational. In general, it has been found that a fifteen second time delay after the power has been turned on is sufficient to assure the system is fully functional and operational.

By referring to FIG. 5, the construction of a conventional power supply is provided which has been found to be effective in supplying the desired five volt power input to the various components of health monitoring system 20 of the present invention. In this embodiment, the desired five volt power is supplied by regulator 105 which receives the six volts generated by four 1.5 volt batteries and provides the requisite five volt power level.

Whenever switch 106 is closed, regulator 105 is activated and the desired five volt power supply is transmitted to the various components of system 20, as detailed above and depicted in FIG. 4. Although various alternate power supply constructions can be employed, this construction is preferred, particularly with capacitors 107, 108, and 109 being employed to maintain a steady five volt supply.

As is apparent from the foregoing detailed disclosure, the health monitoring system of the present invention can be effectively constructed in a plurality of alternate ways, without departing from the scope of this invention. More sophisticated electronics can be employed as well as less sophisticated circuitry, using such systems as analog oneshot timers. However, it is intended that all constructions employing the overall teaching of the present invention are within the scope of this disclosure.

One specific area where many alternate configurations can be used is alarm 27. If desired, a speaker or piezoelectric transducer can be used to create an audible alarm and/or an LED or light bulb can be used for a visual alarm. If desired, a remote relay system can be used for further enhancement by providing an external alarm system. In this way, an alarm can be remotely located in an alternate location from the monitor system by using either a radio link or hard wire connection.

Additional features that may be incorporated into the system, without departing from the scope of the invention, are the use of a low battery indicator in order to increase the system's reliability. A conventional LED or light member can be employed for flashing activation whenever a low battery signal is realized. Alternatively, a unique tone can be generated to inform the user that a low battery condition has been detected.

In a further alternate construction, automatic power on circuitry may be incorporated into the system which is initiated by the placement of an infant in the crib, bassinet, or playpen incorporating passive sensor 21. In this construction, several initial amplifier stages are employed and continuously activated using minor power requirements from the battery. These amplifiers are responsive to a signal generated from the infant being placed on the passive sensor to automatically activate the entire system from its standby mode into its fully powered mode.

Furthermore, circuitry may be incorporated into the system for determining the operational condition of the passive sensor. In this way, an indicator could be incorporated into the system for informing the user when the passive sensor has been torn, punctured, or otherwise damaged.

It will thus be seen that the objects set forth above, among those made apparent from the preceding description, are efficiently attained and, since certain changes may be made in the above constructions without departing from the scope of this invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Having described our invention, what we claim is new and desire to secure by Letters Patent is:

1. An infant health monitoring system for continuously monitoring the overall health of an infant and producing an alarm whenever the health of the infant is in jeopardy, said system comprising:

A. a passive sensor comprising an enlarged sheet formed from material responsive to pressure for producing an output signal proportional to the pressure applied thereto;

B. a first signal processing circuit for monitoring large motor activity of an infant and comprising
      a. means for receiving the output signal from the passive sensor;
      b. a comparator for receiving the output signal receiving means for receiving the output signal therefrom and constructed for comparing the received signal to a reference signal representing normal large motor activity anticipated for an infant and transmitting a motor activity detected output whenever the signal received by the comparator exceeds a reference level; and
      c. a pulse detector/timer
         1. connected to the comparator for receiving the motor activity detected output from the comparator,
         2. timing a period of time between the receipt of the output from said comparator, and
         3. generating an anomaly detected signal whenever the period of time exceeds 40 seconds;

C. a second processing circuit for monitoring breathing rates of an infant and comprising
      a. means for receiving the output signal from the passive sensor;
      b. band pass filter means connected to said output signal receiving means and constructed for receiving the signal from the passive sensor as an input signal thereto and transmitting an output signal corresponding to a range of frequencies representative of a normal breathing rate for infants as detected in the input signal thereto;
      c. a comparator connected to the band pass filter means for receiving the output signal therefrom and constructed for comparing the signal from the band pass filter means to a reference signal representing a normal breathing rate for an infant and transmitting a breathing rate detected output whenever the signal received by the comparator exceeds the reference signal; and
      d. a pulse detector/timer
         1. connected to the comparator for receiving the breathing rate detected output from the comparator,
         2. timing a period of time between the receipt of the output from said comparator, and
         3. generating an anomaly detected signal whenever the period of time exceeds 30 seconds;

D. a third signal processing circuit for monitoring heart rates of an infant and comprising
      a. means for receiving the output signal from the passive sensor,
      b. band pass filter means connected to said output signal receiving means and constructed for receiving the signal from the passive sensor as an input signal thereto and transmitting an output signal corresponding to a range of frequencies representative of a normal heart rate for infants as detected in the input signal thereto;
      c. a comparator connected to the band pass filter means for receiving the output signal therefrom and constructed for comparing the signal from the band pass filter means to a reference signal representing a normal heart rate for an infant and transmitting a heart rate detected output whenever the signal received by the comparator exceeds the reference level; and
      d. a pulse detector/timer
         1. connected to the comparator for receiving the heart rate detected output from the comparator,
         2. timing a period of time between the receipt of the output from said comparator, and
         3. generating an anomaly detected signal whenever the period of time exceeds 30 seconds; and E. control means for receiving the anomaly detected signals from each of the signal processing circuits, determining when an alarm condition exists and transmitting an alarm initiation signal when required.

2. The infant health monitoring system defined in claim 1, wherein said system is further defined as comprising startup delay means constructed for preventing the activation of an alarm signal for a preset period of time, thereby assuring that all components of the system are capable of being properly activated and are operational before an alarm signal can be generated.

3. The infant health monitoring system defined in claim 1, wherein said system further comprises alarm means interconnected to the control means and constructed for receiving the alarm initiation signal therefrom and initiating an alarm signal for providing a desired warning that the infant being monitored may be in jeopardy.

4. The infant health monitoring system defined in claim 1, wherein said control means is further defined as comprising a microprocessor constructed for receiving the detected signals from each of the signal processing circuits, evaluating each of the detected signals signals and determining when an alarm condition exists requiring the transmission of an alarm initiation signal.

5. The infant health monitoring system defined in claim 1, wherein said passive sensor is further defined as being formed from PVDF.

* * * * *